United States Patent
Kang et al.

(10) Patent No.: US 9,417,168 B2
(45) Date of Patent: Aug. 16, 2016

(54) FATIGUE TESTING

(71) Applicant: DMAR ENGINEERING, INC., Houston, TX (US)

(72) Inventors: Yongtian Kang, Qingdao (CN); Dagang Zhang, Houston, TX (US); Zhiming Huang, Missouri City, TX (US); Quan Yuan, Qingdao (CN)

(73) Assignee: DMAR Engineering, Inc., Houston, TX (US)

( * ) Notice: Subject to any disclaimer, the term of this patent is extended or adjusted under 35 U.S.C. 154(b) by 19 days.

(21) Appl. No.: 14/500,918

(22) Filed: Sep. 29, 2014

(65) Prior Publication Data

US 2015/0253228 A1    Sep. 10, 2015

Related U.S. Application Data

(60) Provisional application No. 61/950,222, filed on Mar. 10, 2014.

(51) Int. Cl.
| | |
|---|---|
| *G01N 3/08* | (2006.01) |
| *G01N 3/20* | (2006.01) |
| *G01N 3/22* | (2006.01) |
| *G01N 3/32* | (2006.01) |

(52) U.S. Cl.
CPC .. *G01N 3/20* (2013.01); *G01N 3/08* (2013.01); *G01N 3/22* (2013.01); *G01N 3/32* (2013.01); *G01N 2203/0021* (2013.01); *G01N 2203/0023* (2013.01); *G01N 2203/0037* (2013.01); *G01N 2203/0073* (2013.01); *G01N 2203/0274* (2013.01)

(58) Field of Classification Search
CPC .............. G01N 3/20; G01N 3/08; G01N 3/22
USPC .................... 73/849, 834, 856, 847
See application file for complete search history.

(56) References Cited

U.S. PATENT DOCUMENTS

| | | | | |
|---|---|---|---|---|
| 2,855,801 A * | 10/1958 | Brauer | ...................... | G01N 3/02 73/809 |
| 4,677,856 A * | 7/1987 | Fischer | ...................... | G01N 3/00 73/850 |
| 5,231,882 A * | 8/1993 | Bertele | ...................... | G01N 3/32 73/852 |
| 5,277,069 A * | 1/1994 | Cussac | ...................... | G01N 3/18 73/853 |
| 5,503,024 A * | 4/1996 | Bechtel | ...................... | G01N 3/20 73/849 |
| 5,528,942 A * | 6/1996 | Baratta | ...................... | G01N 3/02 73/818 |
| 5,606,134 A * | 2/1997 | Stieber | ...................... | G01N 3/20 73/849 |
| 5,679,885 A * | 10/1997 | Lenormand | ......... | G01N 15/0826 73/152.06 |
| 6,023,980 A * | 2/2000 | Owen | ...................... | G01N 3/38 73/797 |
| 6,718,833 B2 * | 4/2004 | Xie | ...................... | G01N 3/32 73/789 |
| 6,813,960 B1 * | 11/2004 | Owen | ...................... | G01N 3/32 73/794 |
| 2002/0017144 A1 * | 2/2002 | Miles | ...................... | G01N 3/32 73/808 |
| 2009/0188330 A1 * | 7/2009 | Kindersley | ............... | G01N 3/56 73/862.21 |
| 2013/0247680 A1 * | 9/2013 | Ota | ...................... | G01N 3/12 73/788 |

* cited by examiner

*Primary Examiner* — Max Noori
(74) *Attorney, Agent, or Firm* — Liaoteng Wang

(57) ABSTRACT

Apparatus and methods related to fatigue testing are described. For example, some embodiments may contain a terminal fixer, a terminal support, a bending machine, and a stress-strain collector, and may be used for testing fatigue properties of offshore pipes, risers and their connectors. Some embodiments may be used to apply extruding, twisting and high frequency bending to the testing sample during one testing period, so that the various fatigue properties of the testing sample can be obtained.

16 Claims, 5 Drawing Sheets

FATIGUE TESTING

CROSS REFERENCE TO RELATED APPLICATIONS

This application claims the benefit of U.S. Provisional App. No. 61/950,222, filed on Mar. 10, 2014, which is incorporated herein by reference.

FIELD OF PRESENT DISCLOSURE

This present disclosure relates to fatigue testing.

BACKGROUND INFORMATION

Engineering testing machines are widely used for engineering and industrial products. In the field of offshore engineering products, for example, offshore pipes, risers and their connectors, fatigue testing plays an important role in ensuring materials with proper fatigue strength are used to avoid fatigue failures. By using a fatigue testing system, fatigue endurance properties of the product samples can be directly manifested, and superiorities and defects of the product samples can be discovered, so that appropriate actions can be taken to improve and optimize the engineering products based on the engineering requirements.

DETAILED DESCRIPTION

Figure 1:
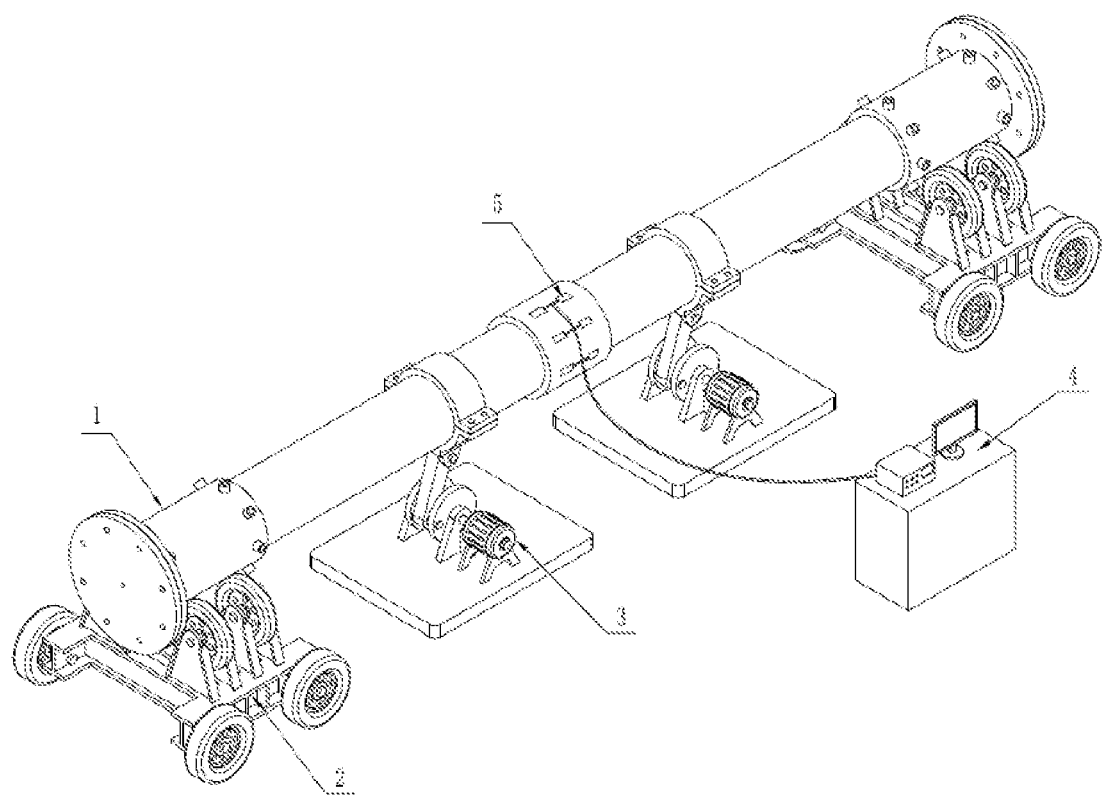
FIG. 1 is an isometric view of an integrated fatigue testing system in one or more embodiments of the present disclosure.

This document discloses apparatus and methods related to fatigue testing. FIG. 1 shows a diagram of an implementation of the apparatus and methods for fatigue testing, which can have a pair of terminal fixer 1, a pair of terminal support 2, two bending machines 3, and a stress-strain collector 4. The stress-strain collector 4 can have a sensor 5, such as a strain gage set for measuring strain, attached to the testing sample, which can be a sample pipe and fixed by the pair of terminal fixers 1 at both ends.

Figure 2:
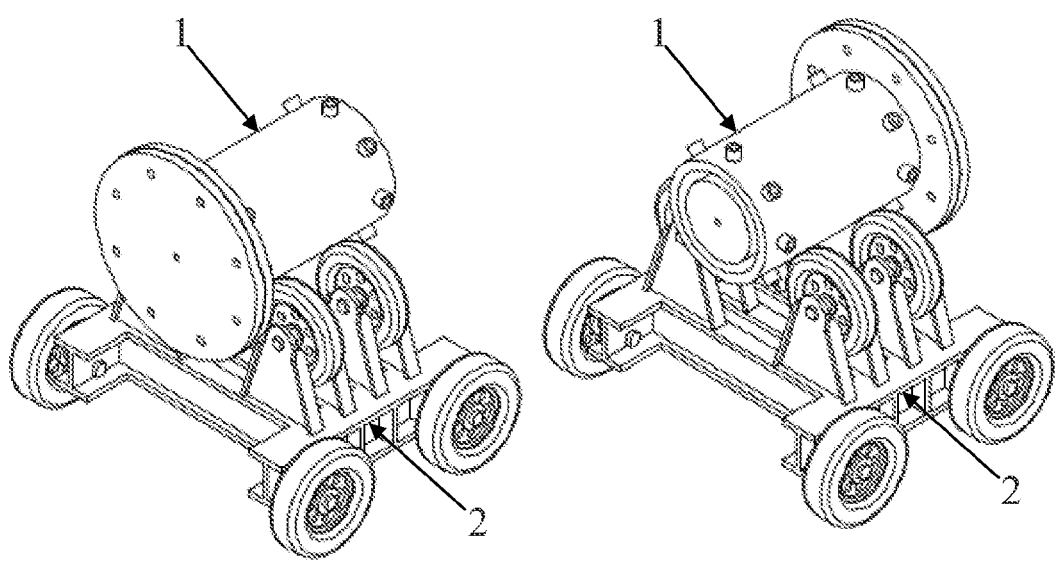
FIG. 2 is an isometric view of the assembly of terminal fixer and terminal support in one or more embodiments of the present disclosure.

FIG. 2 shows an isometric view of an implementation of the assembly of the terminal fixer 1 and terminal support 2, where the terminal fixer 1 is supported by a set of wheels on the terminal support 2 on transverse direction, on which the terminal fixer 1 can be rotated so that twisting force can be applied to the testing sample for torsional fatigue testing. The terminal support 2 can have another set of wheels on longitudinal direction, so that it can also be used for tensile fatigue testing, and can be used for the transport of testing sample.

Figure 3:
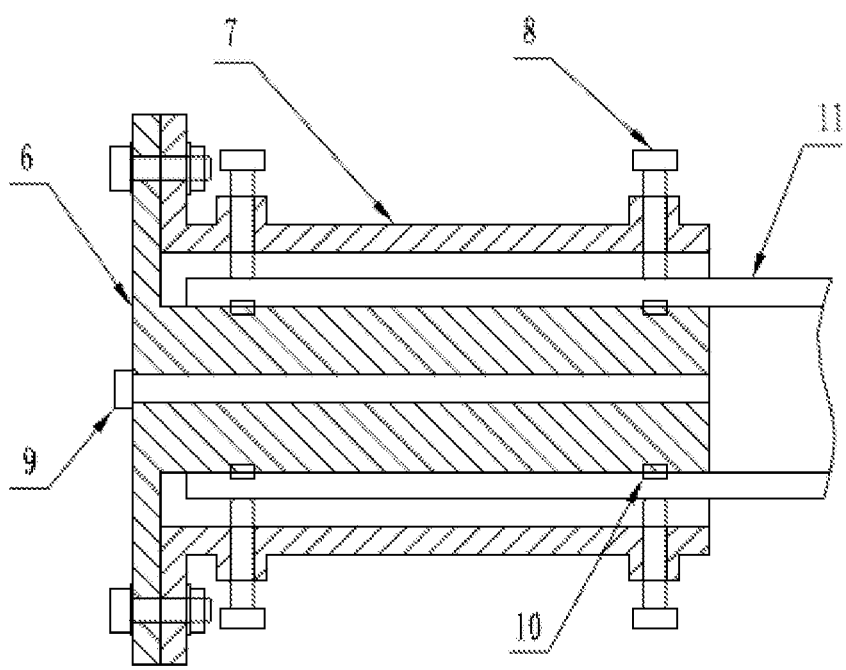
FIG. 3 is a longitudinal cross sectional view of the terminal fixer in one or more embodiments of the present disclosure.

FIG. 3 shows a longitudinal cross sectional view of an implementation of the terminal fixer 1, which comprises an inner liner cylinder 6, a set of screws 8 for tightening the testing sample 11 to the inner liner cylinder 6, which can be customized depending on the dimensions of the testing sample to provide better fitting, and an outer hollow cylinder 7, in which the inner cylinder 6 is aligned and can be attached to, through various fastening means such as the screws 8. The testing sample 11 can be a sample pipe. The inner cylinder 6 can have a pressure port with a quick connector 9. The packing ring 10 can be arranged between the inner cylinder 6 and the sample pipe to create a tight seal. Pressurized liquid can be filled in the sample pipe. Tension and torque can be applied to the testing sample 11 through the flanges on the terminal fixer 1 by connecting the terminal fixer 1 with an external driver via the flanges.

Figure 4:
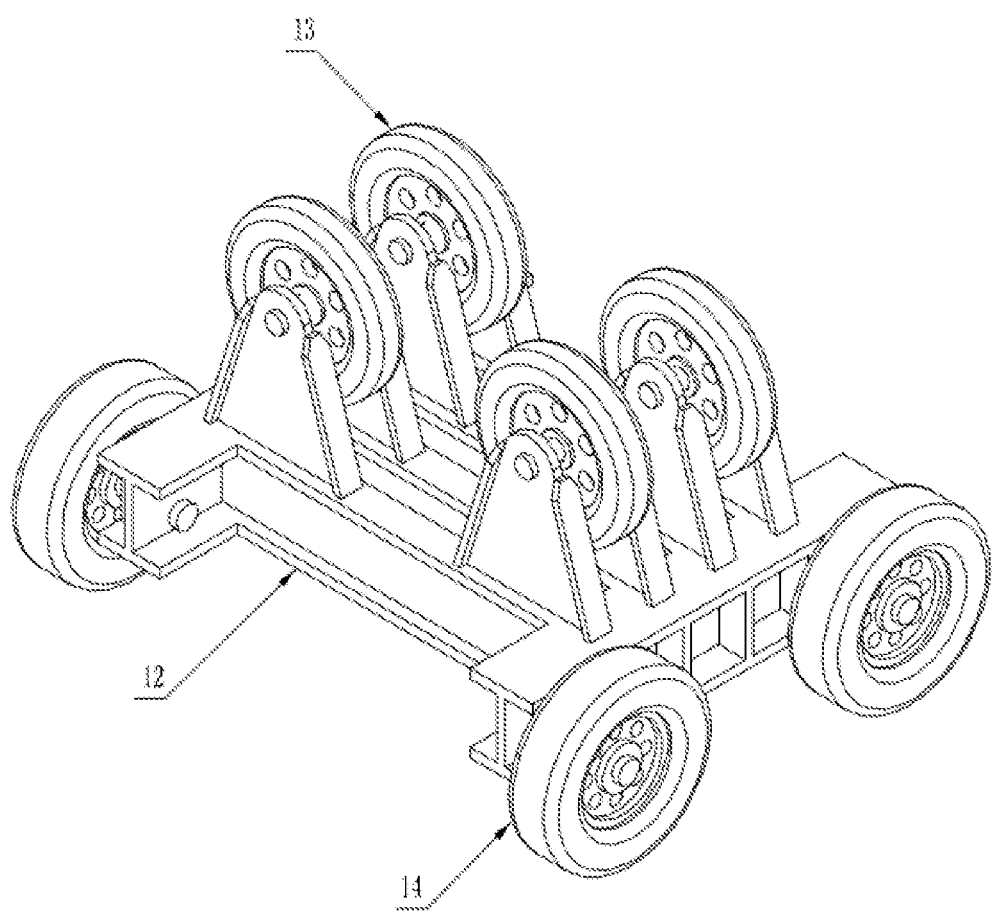
FIG. 4 is an isometric view of the terminal support in one or more embodiments of the present disclosure.

FIG. 4 shows an isometric view of an implementation of the terminal support 2, which can have a main body 12, transverse direction wheel set 13, and longitudinal direction wheel set 14. Each wheel set 13 can contain four wheels, each with a tire mounted on it to avoid rigid contact with the terminal fixer 1. The longitudinal direction wheel set 14 can support and facilitate movement of the main body 12, and the transverse direction wheel set 13 can support the testing sample 11 through the terminal fixer 1, through which the testing sample 11 can be rotated, stretched, and transported, without incurring sliding friction between the testing sample 11 and the external driver.

Figure 5:
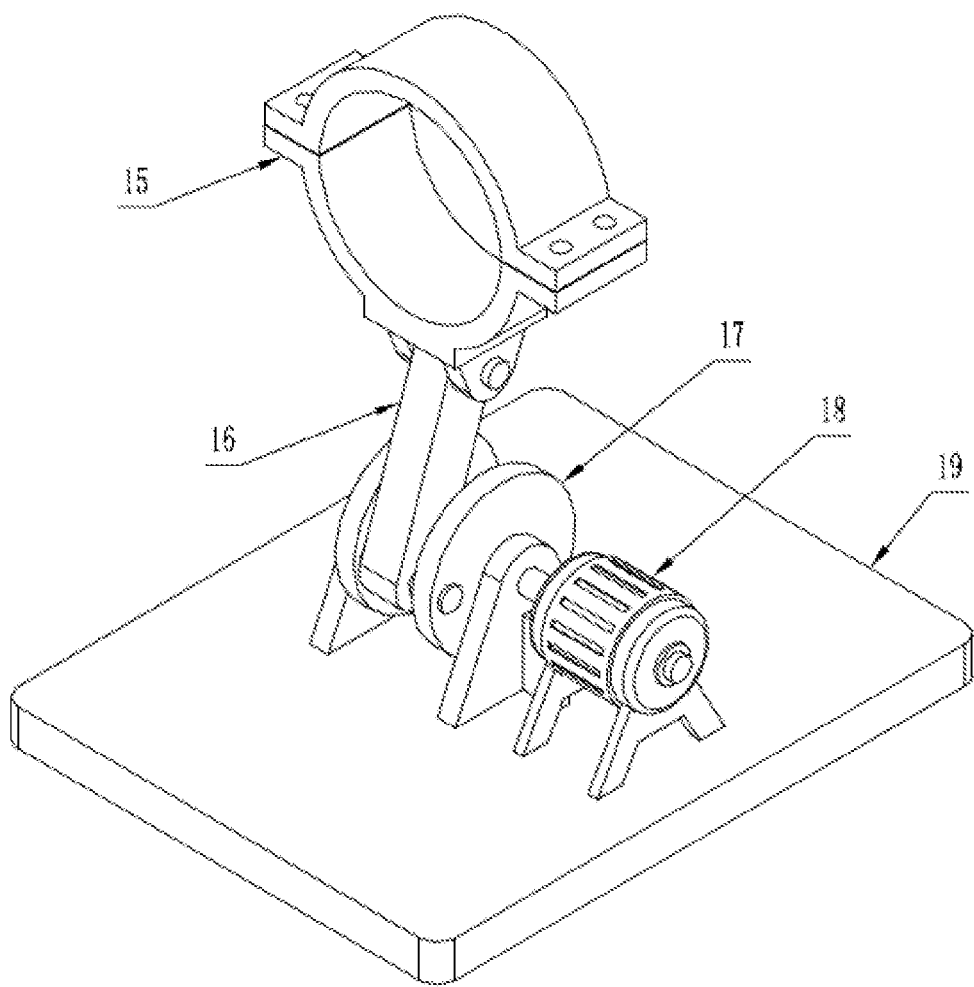
FIG. 5 is an isometric view of the bending machine in one or more embodiments of the present disclosure.

FIG. 5 shows an isometric view of an implementation of the bending machine 3, which comprises a fixture 15, a drive rod 16, a pair of flywheels 17, an electric motor 18, and a machine foundation 19. The fixture 15 can clamp the testing sample 11 with screws on both sides of the upper potion and the lower portion of the fixture 15. Soft liner can be arranged between the fixture 15 and testing sample 11 to avoid rigid contact. The fixture 15 can also be customized for different testing samples 11. The lower portion of the fixer 15 is connected to the drive rod 16 with a shaft. The drive rod 16 is connected at the other end to the flywheels 17, which can be driven by the connected electric motor 18 that can be attached to the machine foundation 19. The electric motor 18 can drive the fixture 15 to move up and down so that the testing sample 11 can be bent easily. By controlling the speed of the electric motor 18 and the length of drive rod 16, different bending amplitude and frequency of the testing sample 11 can be achieved.

More than one bending machine 3 can be included in a fatigue testing system for different forms of bends. For three-point bending setup (such as for pipes), one bending machine can be used. For four-point bending setup (such as for connectors), two bending machines can be used.

The stress-strain collector 4, as shown in FIG. 1, can comprise a computer, a strain tester and a sensor. The strain tester can collect the stress-strain data from the sensor arranged on the testing sample and transmit the data to the computer. Collected data can be processed and analyzed on the computer using the suitable software so that the fatigue properties of the testing sample 11 can be obtained.

OTHER EMBODIMENTS

Various other adaptations and combinations of features of the embodiments and implementations disclosed are within the scope of the present disclosure. It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An apparatus for fatigue testing a sample, comprising:
two terminal fixers configured to fit two ends of the sample, wherein
   at least one terminal fixer from the two terminal fixers comprises an outer cylinder and an inner cylinder; and
   the inner cylinder comprises a pressure port with a quick connector configured to fill the sample with a fluid;
two terminal supports configured to support the two terminal fixers;
a bending machine configured to couple to a part of the sample between the two terminal fixers to bend the sample; and
a stress-strain collector configured to collect data from the sample.

2. An apparatus according to claim 1, wherein at least one terminal fixer from the two terminal fixers is connected to an external driver configured to apply tension and torque to the sample through the at least one terminal fixer.

3. An apparatus according to claim 2, wherein the at least one terminal fixer is connected to the external driver via flanges of the at least one terminal fixer.

4. An apparatus for fatigue testing a sample, comprising:
two terminal fixers configured to fit two ends of the sample, wherein:
   at least one terminal fixer from the two terminal fixers comprises an outer cylinder and an inner cylinder; and
   the at least one terminal fixer further comprises a packing ring arranged between the inner cylinder and the sample to create a tight seal;
two terminal supports configured to support the two terminal fixers;
a bending machine configured to couple to a part of the sample between the two terminal fixers to bend the sample; and
a stress-strain collector configured to collect data from the sample.

5. An apparatus according to claim 4, wherein the sample is a pipe filled with pressurized liquid.

6. An apparatus for fatigue testing a sample, comprising:
two terminal fixers configured to fit two ends of the sample;
two terminal supports configured to support the two terminal fixers, wherein each of the two terminal supports comprises:
   a main body;
   a transverse direction wheel set; and
   a longitudinal direction wheel set;
a bending machine configured to couple to a part of the sample between the two terminal fixers to bend the sample; and
a stress-strain collector configured to collect data from the sample.

7. An apparatus for fatigue testing a sample, comprising:
two terminal fixers configured to fit two ends of the sample;
two terminal supports configured to support the two terminal fixers;
a bending machine configured to couple to a part of the sample between the two terminal fixers to bend the sample, wherein the bending machine comprises:
   a fixture configured to clamp onto the sample;
   a pair of flywheels;
   a drive rod connected to the fixture and the pair of flywheels;
   an electric motor configured to turn the pair of flywheels; and
   a machine foundation, wherein the pair of flywheels and the electric motor are mounted on the machine foundation; and
a stress-strain collector configured to collect data from the sample.

8. An apparatus according to claim 1, wherein the stress-strain collector comprises:
a sensor configured to be placed on the sample;
a computer; and
a strain tester connected to the sensor and the computer.

9. A method for fatigue testing a sample, comprising:
attaching the sample at its two ends to two terminal fixers, which rest on two terminal supports, wherein:
   at least one terminal fixer comprises an outer cylinder and an inner cylinder; and
   the at least one terminal fixer further comprises a packing ring arranged between the inner cylinder and the sample to create a tight seal;
attaching a bending machine to a part of the sample between the two terminal fixers;
attaching a stress-strain collector to the sample;
bending the sample using the bending machine; and
collecting stress-strain data using the stress-strain collector.

10. A method according to claim 9, further comprising:
connecting at least one terminal fixer from the two terminal fixers to an external driver configured to apply tension and torque to the sample through the at least one terminal fixer.

11. A method according to claim 10, wherein the at least one terminal fixer is connected to the external driver via flanges of the at least one terminal fixer.

12. A method according to claim 9, wherein the inner cylinder comprises a pressure port with a quick connector configured to fill the sample with a fluid.

13. A method according to claim 9, wherein the sample is a pipe and the method further comprises filling the pipe with a pressurized liquid.

14. A method for fatigue testing a sample, comprising:
attaching the sample at its two ends to two terminal fixers, which rest on two terminal supports, wherein each of the two terminal supports comprises:
   a main body;
   a transverse direction wheel set; and
   a longitudinal direction wheel set;
attaching a bending machine to a part of the sample between the two terminal fixers;
attaching a stress-strain collector to the sample;
bending the sample using the bending machine; and
collecting stress-strain data using the stress-strain collector.

15. A method for fatigue testing a sample, comprising:
attaching the sample at its two ends to two terminal fixers, which rest on two terminal supports;
attaching a bending machine to a part of the sample between the two terminal fixers, wherein the bending machine comprises:
   a fixture configured to clamp onto the sample;
   a pair of flywheels;
   a drive rod connected to the fixture and the pair of flywheels;
   an electric motor configured to turn the pair of flywheels; and
   a machine foundation, wherein the pair of flywheels and the electric motor are mounted on the machine foundation;

attaching a stress-strain collector to the sample;
bending the sample using the bending machine; and
collecting stress-strain data using the stress-strain collector.

16. A method according to claim 9, wherein the stress-strain collector comprises:
a sensor configured to be placed on the sample;
a computer; and
a strain tester connected to the sensor and the computer.

* * * * *